United States Patent [19]

Hayashi et al.

[11] Patent Number: 4,995,399
[45] Date of Patent: Feb. 26, 1991

[54] BLOOD PRESSURE MEASURING SYSTEM

[75] Inventors: Ressei Hayashi, Tokyo; Tokuji Hayakawa, Komaki, both of Japan

[73] Assignee: Colin Electronisc Co., Ltd., Japan

[21] Appl. No.: 382,991

[22] Filed: Jul. 21, 1989

[30] Foreign Application Priority Data

Jul. 26, 1988 [JP] Japan .............................. 63-98601[U]

[51] Int. Cl.⁵ ........................ A61B 5/02; A61B 5/0205
[52] U.S. Cl. .................................... 128/680; 128/687; 128/689
[58] Field of Search .......................... 128/672, 677–690

[56] References Cited

U.S. PATENT DOCUMENTS

| | | | |
|---|---|---|---|
| 4,367,752 | 1/1983 | Jimenez et al. | 128/689 |
| 4,397,317 | 8/1983 | Villa-Real | 128/680 |
| 4,469,107 | 9/1984 | Asmar et al. | 128/690 X |
| 4,566,461 | 1/1986 | Lubell et al. | 128/689 X |
| 4,592,364 | 6/1986 | Pinto | 128/672 |
| 4,649,929 | 3/1987 | Weaver et al. | 128/680 |
| 4,819,654 | 4/1989 | Weaver et al. | 128/680 |
| 4,830,018 | 5/1989 | Treatch | 128/677 |
| 4,944,305 | 7/1990 | Takatsu et al. | 128/680 |

FOREIGN PATENT DOCUMENTS 0297146  1/1989  European Pat. Off. .

OTHER PUBLICATIONS

WO85/00279; Weaver et al., 1–1985.
Singer et al., "Outpatient Monitoring with Portable Microprocessor Recording System", Wecson Technical Papers, vol. 19, 9–1975, pp. 1–10.
Yamakoshi et al., "Long-Term Ambul. Monitoring of Indirect Arterial BP Using a Volume Oscillometric Method"; Med. and Biol. Engr., vol. 23, No. 5, 9–1985, pp. 459–465.

*Primary Examiner*—Lee S. Cohen
*Assistant Examiner*—Krista Pfaffle
*Attorney, Agent, or Firm*—Oliff & Berridge

[57] ABSTRACT

A blood pressure measuring system for continuously measuring blood pressure values of a subject, including a measuring device for repetitively measuring a blood pressure value of the subject, a display device for indicating a time-wise trend of the measured blood pressure values, a memory device for storing a plurality of sets of data representing a plurality of predetermined time-wise trends of blood pressure, respectively, a designating device for designating one of the plurality of sets of data, and an indicating device for commanding the display device to indicate, according to the designated one set of data, a corresponding one of the plurality of predetermined time-wise trends of blood pressure, together with the time-wise trend of the measured blood pressure values.

14 Claims, 3 Drawing Sheets

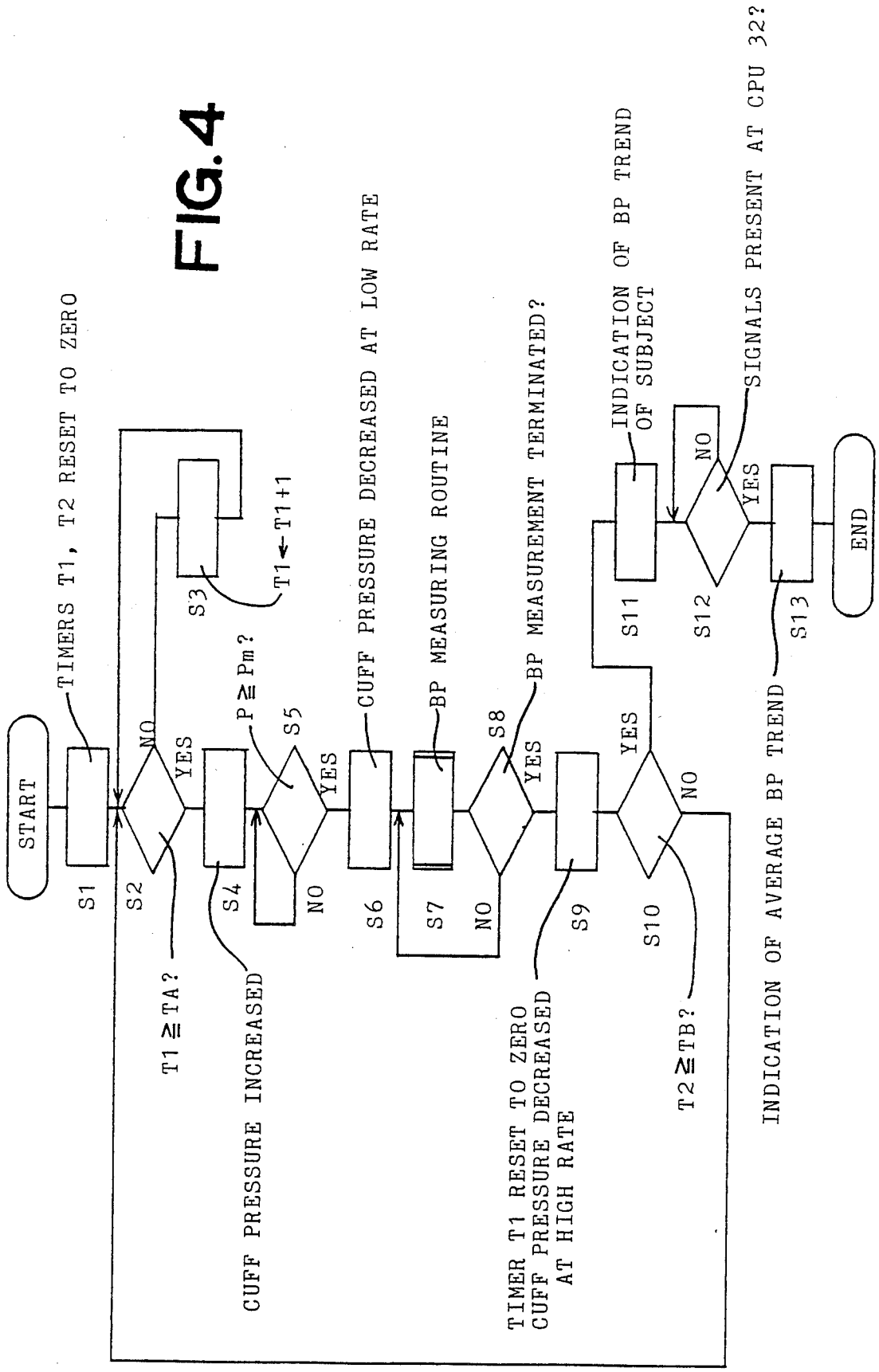

BLOOD PRESSURE MEASURING SYSTEM

BACKGROUND OF THE INVENTION

1. Field of the Art

The present invention generally relates to a blood pressure measuring system and particularly to such a system which continuously measures blood pressure values of a living body and indicates a time-wise trend of the measured blood pressure values.

2. Discussion of the Prior Art

There is known a portable blood pressure measuring device which is kept on a living body or subject for a comparatively long time period, often one day (24 hours), in everyday life, so as to continuously measure blood pressure values of the subject. The measured blood pressure values are indicated or displayed to provide a one-day time-wise trend of blood pressure of the subject. Comparison of the one-day blood pressure variation of the subject with a normal variation of people who have the same characteristics, such as sex and age, as those of the subject, would enable diagnosis on pathology of the blood pressure of the subject.

However, the above conventional device does not permit the above comparison, since the device indicates only the one-day blood pressure variation of the subject. Thus, it has conventionally been difficult to compare the one-day blood pressure variation of a subject with a normal variation of people who have the same characteristics as the subject. In other words, it has been difficult to do prompt and reliable diagnosis on the blood pressure of the subject.

SUMMARY OF THE INVENTION

It is therefore an object of the present invention to provide a blood pressure measuring system which easily permits comparison between a time-wise trend of the actually measured blood pressure values of a subject and a normal time-wise trend of blood pressure.

The above object has been achieved by the present invention, which provides a blood pressure measuring system for continuously measuring blood pressure values of a subject, comprising (a) measuring means for repetitively measuring a blood pressure value of the subject, (b) a display device for indicating a time-wise trend of the measured blood pressure values, (c) memory means for storing a plurality of sets of data representing a plurality of predetermined time-wise trends of blood pressure, respectively, (d) designating means for designating one of the plurality of sets of data, and (e) control means for commanding the display device to indicate, according to the designated one set of data, a corresponding one of the plurality of predetermined time-wise trends of blood pressure, together with the time-wise trend of the measured blood pressure values.

In the blood pressure measuring system constructed as described above, blood pressure measurements are repetitively conducted so that a time-wise trend of the repetitively measured blood pressure values is indicated by the display device, and one of the plurality of sets of data stored in the memory means is designated so that a predetermined time-wise trend of blood pressure is indicated together on the display device according to the designated one set of data. Thus, the time-wise trend of the actually measured blood pressure values of the subject is indicated together with the predetermined time-wise trend represented by the designated one set of data, for example, normal time-wise trend of people who have the same characteristics as those of the subject. Thus, the present system easily permits comparison between the two time-wise trends, thereby enabling prompt and reliable diagnosis on pathology of the blood pressure of the subject.

According to a feature of the present invention, each of the plurality of predetermined time-wise trends of blood pressure is a normal time-wise trend of blood pressure of people who have a same value as to each of at least one parameter. The at least one parameter may comprise age and sex. In this case, the designating means may designate one of the plurality of sets of data which represents a normal time-wise trend of blood pressure of people who have the same age and sex as those of the subject.

According to another feature of the present invention, the system further comprises means for designating one of a plurality of conditions of the subject, means for entering a beginning time and an ending time when the designated condition begins and ends, respectively, and means for modifying the designated one set of data based on the designated condition and the entered beginning and ending times. The plurality of conditions of the subject may comprise a first condition in which the subject is having a meal, a second condition in which the subject is out of doors, a third condition in which the subject is using a bath, and a fourth condition in which the subject is in bed.

According to yet another feature of the present invention, the display device indicates the corresponding one predetermined time-wise trend, together with the time-wise trend of the measured blood pressure values, in a two-dimensional table defined by a first axis indicative of time and a second axis indicative of blood pressure.

According to a further feature of the present invention, the measuring means repetitively measures a blood pressure value of the subject for a predetermined time period. The predetermined time period may be 24 hours. The display device may indicate the time-wise trend of the measured blood pressure values and the corresponding one predetermined time-wise trend, after the predetermined time period has elapsed.

According to a still further feature of the present invention, each time the measuring means measures a blood pressure value of the subject, the display device concurrently indicates the measured blood pressure value and thereby progressively produces the time-wise trend of the measured blood pressure values.

In an embodiment of the present invention, the measuring means repetitively measures a blood pressure value of the subject at regular time intervals of 5 to 30 minutes.

In another embodiment of the present invention, the measuring means repetitively measures a maximum and a minimum blood pressure value of the subject, the display device indicating a time-wise trend of the measured maximum and minimum blood pressure values, each of the plurality of sets of data representing a predetermined time-wise trend of maximum and minimum blood pressure.

In yet another embodiment of the present invention, the measuring means comprises a memory card for storing a set of data representing the measured blood pressure values of the subject, the measuring means being separate from the display device, the memory means, the designating means and the indicating means, the display device indicating the time-wise trend of the measured blood pressure values according to the set of data stored in the memory card.

BRIEF DESCRIPTION OF THE DRAWINGS

The above and optional objects, features and advantages of the present invention will be better understood by reading the following detailed description of the presently preferred embodiment of the invention, when considered in conjunction with the accompanying drawings, in which:

FIG. 4 is a flow chart illustrating the operation of the system of FIG. 1.

DETAILED DESCRIPTION OF THE PREFERRED EMBODIMENT

Figure 1:
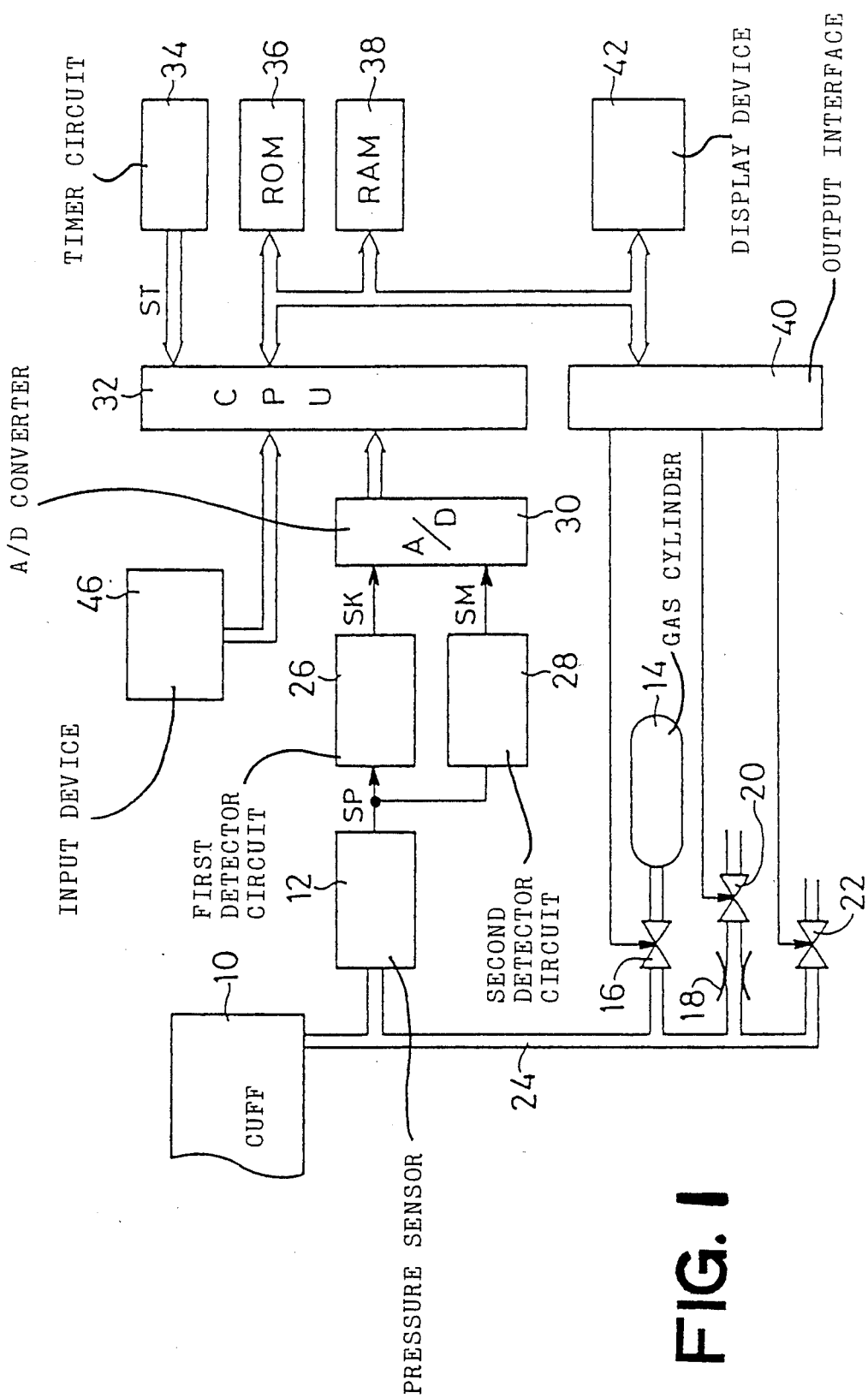
FIG. 1 is a diagrammatic view of a blood pressure measuring system embodying the present invention.

Referring first to FIG. 1 there is diametrically illustrated a portable blood pressure measuring system embodying the present invention. The present system is adapted to continuously measure blood pressure values of a living body or subject for a comparatively long time, for example one day or 24 hours. In the figure, reference numeral 10 designates an inflatable cuff which is formed of rubber and has a bag-like structure. The cuff 10 is wound around an upper arm of the subject. The cuff 10 is connected via a piping 24 to a pressure sensor 12, a gas cylinder 14, a first electromagnetic valve 16, a second electromagnetic valve 20 with a restrictor 18, and a third electromagnetic valve 22. The gas cylinder 14 is charged with compressed carbonic-acid gas. The first valve 16 opens and closes the gas cylinder 14. The second valve 20 with the restrictor 18 serves to decrease the fluid pressure in the cuff 10 at a comparatively low rate. The third valve 22 serves to decrease the fluid pressure at a comparatively high rate. The pressure sensor 12 detects time-wise variation in the fluid pressure of the cuff 10, and generates a pressure signal SP representing the detected fluid pressure variation, to a first and a second detector circuit 26, 28. The first detector circuit 26 includes a low-pass filter and, upon reception of pressure signal SP, generates a cuff-pressure signal SK representing variation in static pressure of the fluid pressure of the cuff 10, to a central processing unit (CPU) 32 via an analog/digital (A/D) converter 30. Meanwhile, the second detector circuit 28 includes a band-pass filter which selectively transmits, as a pulse-wave signal SM, frequency components in a frequency range which covers frequencies of pulse wave, i.e., pressure oscillation produced in the cuff 10 in synchronization with pulsation of the heart of the subject. Upon reception of pressure signal SP, the second detector circuit 28 supplies pulse-wave signal SM to the CPU 32 via the A/D converter 30.

The CPU 32 is coupled via data bus to a read-only memory (ROM) 36, a random access memory (RAM) 38, an output interface 40, and a display device 42. Also, the CPU 32 is coupled to a timer circuit 34, so that the CPU 32 is supplied with a time signal ST. The CPU 32 processes the received signals according to software programs pre-stored in the ROM 36 by utilizing the temporary-storage function of the RAM 38, and generates command signals via the output interface 40 to open and close the first, second and third electromagnetic valves 16, 20, 22. In this way, the CPU 32 operates to continuously measure blood pressure values of the subject. More specifically described, the CPU 32 operates to periodically measure a blood pressure value of the subject based on pulse-wave signal SM and cuff-pressure signal SK, and successively store in the RAM 38 the data indicative of the measured blood pressure values, together with the data indicative of the times of measurement of those blood pressure values. These data will be referred to as the "BP-measurement" data. After the continuous blood pressure measurement has ended, namely 24 hours after the beginning thereof, the CPU 32 commands the display device 42 to indicate, according to the BP-measurement data stored in the RAM 38, a time-wise trend of the measured blood pressure values all at once.

In the ROM 36 are stored a plurality of sets of data each of which represents a normal time-wise trend of blood pressure. Each normal time-wise trend of blood pressure stored may be predetermined based on a mean value of the blood pressure values of many people who have a same or common value as to each of physical characteristics or parameters such as age and sex. In this case, the relationship between age and its value may be such that ages themselves are used as their values. Alternatively, the relationship may be such that 0 to 9 year old correspond to one, 10 to 19 year old correspond to two, 20 to 29 year old correspond to three, and so on. The relationship between sex and its value may be such that male correspond to one and female correspond to two. Each of the normal time-wise trends consists of trends of maximum and minimum blood pressures. In the present embodiment, the ROM 36 serves as the memory means for storing the sets of data representing the predetermined time-wise trends of blood pressure.

Figure 2:
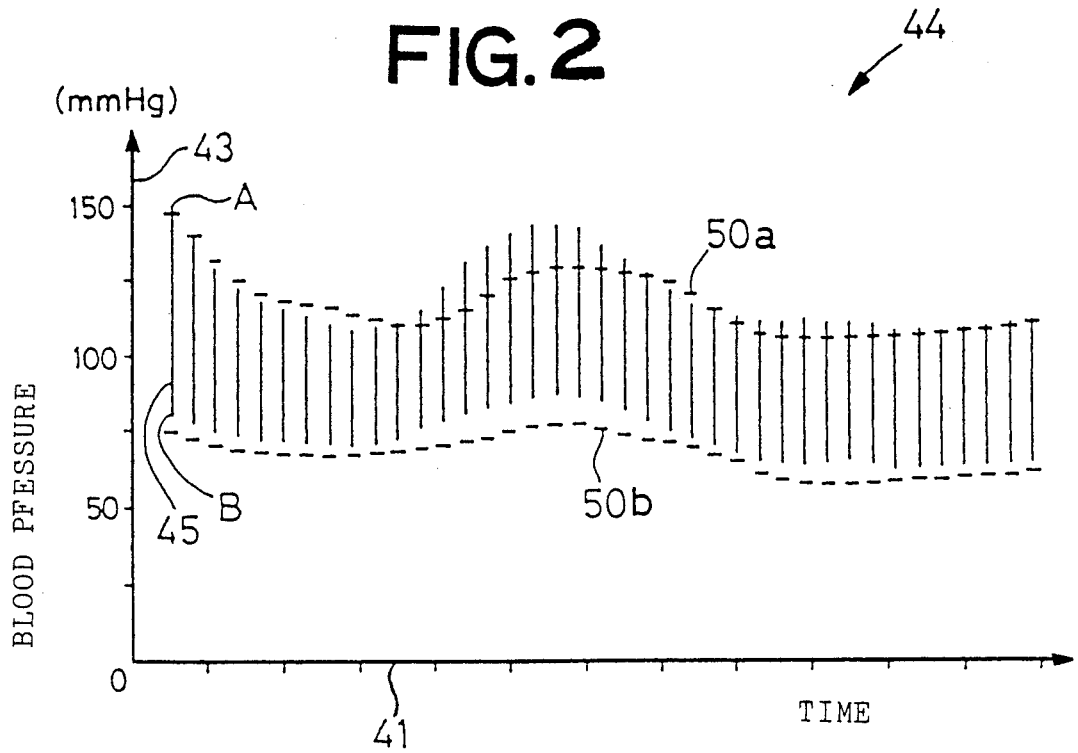
FIG. 2 is a graph provided on a display device of the system of FIG. 1, showing a time-wise trend of the actually measured blood pressure values of a subject and a normal time-wise trend of blood pressure, the two time-wise trends being compared with each other.

The display device 42 includes a cathode ray tube which has thereon a two-dimensional table 44 defined by the axis of abscissa 41 indicative of time and the axis of ordinate 43 indicative of blood pressure (mmHg) as shown in FIG. 2. Upon reception of a display signal from the CPU 32, the display device 42 indicates, in the two-dimensional table 44, bars 45 each of which represents a maximum and a minimum blood pressure value at an upper and a lower end A, B thereof, respectively.

Figure 3:
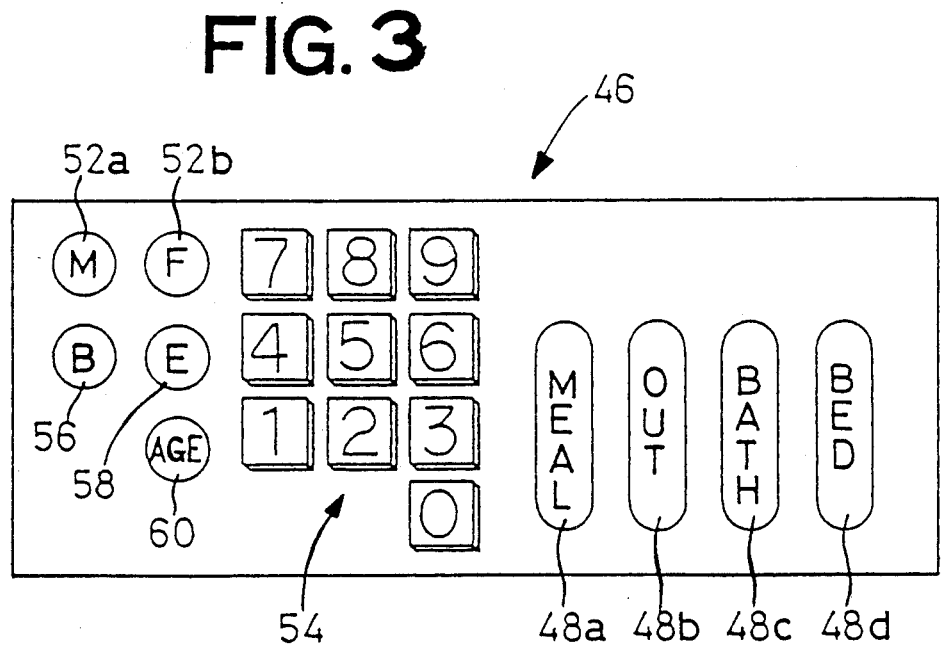
FIG. 3 is a schematic plan view of an input device of the system of FIG. 1.

Referring next to FIG. 3 there is shown an input device 46 having various keys. Two sex keys, i.e., male and female keys 52a, 52b are used to designate the sex of the subject. Upon operation of one of the sex keys 52a, 52a, a signal representing the designated sex is supplied to the CPU 32. An age key 60 and ten numeral keys 54 are used to designate the age of the subject. Upon operation of appropriate ones of the numeral keys 54 after operation of the age key 60, a signal representing the designated age is supplied to the CPU 32. Four condition keys 48a, 48b, 48c, 48d are used to designate one of four conditions which the subject can take. The "MEAL" key 48a corresponds to the condition in which the subject is having a meal; the "OUT" key 46b corresponds to the condition in which the subject is out of doors; the "BATH" key 48c corresponds to the condition in which the subject is using a bath; and the "BED" key 48d corresponds to the condition in which the subject is in bed. The input device 46 also has a condition-begin key 56 and a condition-end key 58.

When the subject has begun a meal at 8:05 p.m., for example, the subject operates the "MEAL" key 48a, the condition-begin key 56, and the "2", "0" (twice) and "5" keys of the numeral keys 54. Thus, a signal representing what time the subject has begun what condition, is supplied to the CPU 32. Similarly, when the subject has ended the meal at 8:55 p.m., the subject operates the "MEAL" key 48a, the condition-end key 58, and the "2", "0" and "5" (twice) keys of the numeral keys 54. Thus, a signal what time the subject has ended what condition. Alternatively, it is permitted to write down the taken condition and the beginning and ending times thereof and, after a while, enter those data through the input device 46.

Upon entering or designation of the physical characteristics of the subject, namely age and sex through the input device 46, the CPU 32 selects, according to the signals representing the designated sex and age, one of the plurality of sets of data which represents a normal time-wise trend of blood pressure of people who have the same age and sex as the subject. The CPU 32 also modifies the selected one set of data based on the designated one or more conditions and the beginning and ending times thereof. Since people usually take during one day two or more conditions out of the four conditions specified in the present embodiment, the CPU 32 modifies the designated one set of data based on each of the two or more conditions. Thus, as shown in FIG. 2, the modified normal time-wise trend of maximum and minimum blood pressures, represented by the modified, selected one set of data, is indicated in a pair of broken curves 50a, 50b in the two-dimensional table 44, together with the time-wise trend (i.e., successive bars 45) of the actually measured maximum and minimum blood pressure values. The upper broken curve 50a represents the normal time-wise trend of maximum blood pressure, while the lower broken curve 50b represents the normal time-wise trend of minimum blood pressure. In the present embodiment, the input device 46 serves as the means for designating one of the sets of data stored in the ROM 36, while the CPU 32 cooperates with the ROM 36, RAM 38 and others to serve as the means for commanding the display device 42 to indicate a predetermined time-wise trend according to the designated one set of data.

There will be described the operation of the above-described blood pressure measuring system, by reference to the flow chart of FIG. 4.

Upon supply of electric power to the present system and subsequent operation of a START button (not shown), in step S1 is implemented the initialization of the system in which a first and a second time counter T1, T2 are reset to zero. The first time counter T1 has a reference value TA which corresponds to the regular time interval of the periodic blood pressure measurements effected in the present system. In the present embodiment, reference value TA is predetermined at 5 to 30 minutes. The second time counter T2 has a reference value TB which corresponds to the time period of the continuous blood pressure measurement; 24 hours in the present embodiment. Step S1 is followed by step S2 in which it is judged whether or not the first time counter T1 has counted up to reference value TA. At an early stage of a measuring cycle the judgement in step S2 is negative (NO), and the control of the CPU 32 goes to step S3 in which the counter T1 adds one. Steps S2 and S3 are repeated until the first time counter T1 reaches reference value TA. On the other hand, if the judgement in step S2 is affirmative (YES), then step S4 is effected in which both the second and third electromagnetic valves 18, 22 are closed and the first electromagnetic valve 16 is opened, so that compressed $CO_2$ gas is supplied from the cylinder 14 to the cuff 10, whereby the fluid pressure P in the cuff 10 (hereinafter, referred to as "cuff pressure P") is increased. Step S4 is followed by step S5 in which it is judged whether or not cuff pressure P has exceeded a target pressure Pm. Target pressure Pm is predetermined to be sufficiently higher than an estimated maximum blood pressure of the subject, for example 180 mmHg. If cuff pressure P has not exceeded target pressure Pm, step S5 is repeated. On the other hand, if cuff pressure P has exceeded target pressure Pm, then the control of the CPU 32 goes to step S6 in which the first valve 16 is closed and the second valve 20 with the restrictor 18 is opened, so that cuff pressure P is decreased at a comparatively low rate. Step S6 is followed by step S7, namely, blood pressure measuring routine. In the routine, a value of cuff pressure P, represented by signal SK, at the time when amplitudes of pulses of pulse wave, represented by signal SM, are largely varied for the first time during the low-rate pressure decrease, is determined as a maximum blood pressure of the subject. Meanwhile, a value of cuff pressure P when the amplitudes of pulses of the pulse wave are largely varied for the second time during the low-rate pressure decrease, is determined as a minimum blood pressure of the subject. The data indicative of the measured maximum and minimum blood pressure values is stored in the RAM 38 together with the data indicative of the time of measurement of those values, this time data being produced based on time signal ST supplied from the timer circuit 34. These data accumulate in the RAM 38 to provide the previously-mentioned BP measurement data, in the periodically conducted blood pressure measurements.

Step S7 is followed by step S8 in which it is judged whether or not the blood pressure measurement in step S7 has been completed. At an early stage in the measuring cycle, the measurement has not been completed yet, and steps S7 and S8 are repeated. On the other hand, if the judgement in step S8 is turned affirmative, then the control of the CPU 32 advances to step S9 in which the first time counter T1 is reset to zero, and the third electromagnetic valve 22 is opened to decrease cuff pressure P at a comparatively high rate. Step S9 is followed by step S10 in which it is judged whether or not the second time counter T2 has counted up to reference value TB. At an early stage in the continuous blood pressure measurement, the judgement in step S10 is negative, and the control of the CPU 32 goes back to effect step S2 and the following steps. On the other hand, if the judgement in step S10 is turned affirmative, namely, 24 hours have elapsed since the beginning, then the continuous blood pressure measurement is terminated and the control of the CPU 32 goes to step S11.

In step S11 a time-wise trend of the measured blood pressure values of the subject is indicated all at once on the display device 42, according to the BP measurement data stored in the RAM 38, as shown in FIG. 2. Step S11 is followed by step S12 in which it is judged whether or not all of the signals representing the age and sex of the subject and the designated one or more conditions of the subject, are present at the CPU 32. In the case where the judgement in step S12 is negative, step S12 is repeated. However, if the judgement is affirmative, subsequently step S13 is effected in which is retrieved from the ROM 36 one of the plurality of sets of data which represents a normal time-wise trend of blood pressure corresponding to the age and sex of the subject, and the retrieved set of data is modified by the CPU 32 according to the designated one or more conditions and the beginning and ending times thereof. The display device 42 indicates, according to the modified set of data, the corresponding, modified time-wise trend of blood pressure (i.e., broken curves 50a, 50b), together with the time-wise trend of the measured blood pressure values (i.e., successive bars 45), in the same table 44 provided thereon.

It follows from the foregoing description that, in the illustrated blood pressure measuring system, the time-wise trend of the periodically measured blood pressure values is indicated together with a normal time-wise trend of blood pressure which is selected according to the physical characteristics of the subject entered through the input device 46 and modified according to the designated one or more conditions of the subject, in the same table on the display device 42. Accordingly, the present system easily permits comparison between the two time-wise trends, thereby facilitating diagnosis on pathology of the blood pressure of the subject.

While the present invention has been described in detail in the preferred embodiment thereof, it is to be understood that the invention may be otherwise embodied.

For example, while in the illustrated embodiment the blood pressure measuring means, including the members 10 to 40, is electrically coupled to the display device 42 and input device 46, it is possible to separate blood pressure measuring means from the display device (42) and input device (46). In this case, it is recommended that the blood pressure measuring means be provided with a writing device which is capable of storing data of the measured blood pressure values, on a magnetic memory card. After the continuous blood pressure measurement has ended, the data stored in the memory card is reproduced by a reading device located at a hospital, so as to be indicated like the graph of FIG. 2. Thus, the reading device serves as a display device. Meanwhile, the input device (46) is coupled to the reading device. A plurality of sets of data representing a plurality of normal time-wise trends of blood pressure are stored in memory means provided in the reading device. Similar to the illustrated embodiment, one set of data representing a normal time-wise trend corresponding to the characteristics of the subject, is designated via the input device, and the normal time-wise trend is indicated in comparison with the time-wise trend of the actually measured blood pressure values reproduced according to the data stored in the memory card. This modified system is more advantageous because, when the subject goes out of doors, only the blood pressure measuring means is kept on the body of the subject.

Furthermore, it is possible to use a mean time-wise trend of the subject calculated based on the seven time-wise trends measured during seven days, as the time-wise trend of the actually measured blood pressure values compared with the normal time-wise trend corresponding to the characteristics of the subject.

Moreover, while in the illustrated embodiment the time-wise trend of the periodically measured blood pressure values is indicated at once according to the BP measurement data stored in the RAM 38, after the continuous blood pressure measurement of 24 hours, it is possible that, each time a blood pressure of the subject is measured, the measured blood pressure is concurrently indicated. In this case, the time-wise trend of the measured blood pressure values is progressively produced on the display device (42).

Although in the illustrated embodiment the two parameters, sex and age, are used to designate one of the plurality of normal time-wise trends of blood pressure which corresponds to the characteristics of the subject, it is possible to add one or more parameters relating to blood pressure. Further, in addition to the four conditions, "MEAL", "OUT", "BATH" and "BED" used in the illustrated embodiment to modify the designated one normal time-wise trend, it is possible to employ one or more other conditions which have effect on the blood pressure of the subject.

It is to be understood that the present invention is not limited to the details of the foregoing description, and that the invention may be embodied with various other changes, modifications and improvements that may occur to those skilled in the art without departing from the scope and spirit of the invention defined in the appended claims.

What is claimed is:

1. A blood pressure measuring system for continuously measuring blood pressure values of a subject, comprising
   measuring means for repetitively measuring a blood pressure value of the subject;
   display means for indicating a time-wise trend of the measured blood pressure values;
   memory means for storing a plurality of sets of data representing a plurality of predetermined time-wise trends of blood pressure, respectively;
   designating means for designating one of said plurality of sets of data such that the designated one set of data corresponds to a value of at least one parameter of the subject; and
   control means for commanding said display means to indicate, according to the designated one set of data, a corresponding one of said plurality of predetermined time-wise trends of blood pressure, together with the time-wise trend of said measured blood pressure values.

2. The system as set forth in claim 1, wherein each of said plurality of sets of data stored in said memory means represents a normal time-wise trend of blood pressure of people who have a same value as to each of said at least one parameter.

3. The system as set forth in claim 2, wherein said designating means further comprises means for entering said at least one parameter and wherein said at least one parameter comprises age and sex.

4. The system as set forth in claim 3, wherein said designating means designates one of said plurality of sets of data which represents a normal time-wise trend of blood pressure of people who have the same age and sex as those of the subject.

5. The system as set forth in claim 1, further comprising means for designating one of a plurality of conditions of said subject, means for entering a beginning time and an ending time when the designated condition begins and ends, respectively, and means for modifying said designated one set of data based on the designated condition and the entered beginning and ending times.

6. The system as set forth in claim 5, wherein said means for designating further comprises keying means for entering at least one of said plurality of conditions of said subject wherein said conditions comprise a first condition in which the subject is having a meal, a second condition in which the subject is out of doors, a third condition in which the subject is using a bath, and a fourth condition in which the subject is in bed.

7. The system as set forth in claim 1, wherein said display means indicates said corresponding one predetermined time-wise trend, together with the time-wise trend of said measured blood pressure values, in a two-dimensional table defined by a first axis indicative of time and a second axis indicative of blood pressure.

8. The system as set forth in claim 1, wherein said measuring means repetitively measures a blood pressure value of the subject for a predetermined time period.

9. The system as set forth in claim 8, wherein said predetermined time period is 24 hours.

10. The system as set forth in claim 8, wherein said display means indicates the time-wise trend of said measured blood pressure values and said corresponding one predetermined time-wise trend, after said predetermined time period has elapsed.

11. The system as set forth in claim 1, wherein, each time said measuring means measures a blood pressure value of the subject, said display means concurrently indicates the measured blood pressure value and thereby progressively produces the time-wise trend of said measured blood pressure values.

12. The system as set forth in claim 1, wherein said measuring means repetitively measures a blood pressure value of the subject at regular time intervals of 5 to 30 minutes.

13. The system as set forth in claim 1, wherein said measuring means repetitively measures a maximum and a minimum blood pressure value of the subject, said display means indicating a time-wise trend of the measured maximum and minimum blood pressure values, each of said plurality of sets of data representing a predetermined time-wise trend of maximum and minimum blood pressure.

14. The system as set forth in claim 1, wherein said measuring means comprises a memory card for storing a set of data representing said measured blood pressure values of the subject, said measuring means being separate from said display means, said memory means, said designating means and said control means, said display means indicating the time-wise trend of said measured blood pressure values according to said set of data stored in said memory card.

* * * * *